United States Patent
Kinn et al.

(10) Patent No.: US 7,989,672 B2
(45) Date of Patent: Aug. 2, 2011

(54) PROCESS AND APPARATUS FOR PARA-XYLENE PRODUCTION

(75) Inventors: Timothy F. Kinn, Houston, TX (US); Kevin J. Knob, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 600 days.

(21) Appl. No.: 12/042,433

(22) Filed: Mar. 5, 2008

(65) Prior Publication Data

US 2008/0249345 A1    Oct. 9, 2008

Related U.S. Application Data

(60) Provisional application No. 60/921,729, filed on Apr. 4, 2007.

(51) Int. Cl.
*C07C 7/17* (2006.01)
*C07C 5/52* (2006.01)
(52) U.S. Cl. .................. 585/812; 585/816; 585/470
(58) Field of Classification Search .................. None
See application file for complete search history.

(56) References Cited

U.S. PATENT DOCUMENTS

| | | | |
|---|---|---|---|
| 3,662,013 A | 5/1972 | Machell et al. | |
| 4,120,911 A | 10/1978 | Davidson | |
| 5,349,113 A | 9/1994 | Chang et al. | |
| 5,349,114 A | 9/1994 | Lago et al. | |
| 5,365,004 A | 11/1994 | Beck et al. | |
| 5,367,099 A | 11/1994 | Beck et al. | |
| 5,403,800 A | 4/1995 | Beck et al. | |
| 5,448,005 A | 9/1995 | Eccli et al. | |
| 5,455,213 A | 10/1995 | Chang et al. | |
| 5,476,823 A | 12/1995 | Beck et al. | |
| 5,495,059 A | 2/1996 | Beck et al. | |
| 5,498,814 A | 3/1996 | Chang et al. | |
| 5,498,822 A | 3/1996 | Eccli et al. | |
| 5,516,736 A | 5/1996 | Chang et al. | |
| 5,610,112 A | 3/1997 | Lago et al. | |
| 5,633,417 A | 5/1997 | Beck et al. | |
| 5,659,098 A | 8/1997 | Beck et al. | |
| 6,576,582 B1 | 6/2003 | Beck et al. | |
| 6,777,583 B2 | 8/2004 | Beck et al. | |
| 2006/0287563 A1* | 12/2006 | Schultz et al. | ............... 585/481 |

FOREIGN PATENT DOCUMENTS

| | | |
|---|---|---|
| EP | 0 308 096 | 2/1993 |
| WO | 95/26946 | 10/1995 |
| WO | 95/26947 | 10/1995 |
| WO | 99/25791 | 5/1999 |
| WO | 2005/100287 | 10/2005 |

OTHER PUBLICATIONS

Pines, Herman "The Chemistry of Catalytic Hydrocarbon Conversions", Academic Press, Inc. London, 1981, vol. 61, Issue 3, pp. 72-73.

* cited by examiner

*Primary Examiner* — Tam M Nguyen
(74) *Attorney, Agent, or Firm* — Andrew B. Griffis

(57) ABSTRACT

A process of producing PX comprising providing a $C_8+$ feedstock, the $C_8+$ feedstock has $C_8$ hydrocarbons and $C_9+$ hydrocarbons, to a crystallization unit under crystallization conditions to produce a PX enriched stream having a PX concentration of at least 99.5 wt % based on the weight of the PX enriched stream, wherein the $C_8+$ feedstock has a PX concentration of at least 70 wt % based on total weight of xylenes in the $C_8+$ feedstock, which the $C_8+$ feedstock having a $C_9+$ hydrocarbons concentration in a range from 1 wppm to 10 wt % based on the total weight of the $C_8+$ feedstock.

13 Claims, No Drawings

PROCESS AND APPARATUS FOR PARA-XYLENE PRODUCTION

PRIORITY CLAIM

This application claims the benefit of U.S. Provisional Application No. 60/921,729, filed Apr. 4, 2007, the entirety of which is incorporated by reference.

FIELD OF THE INVENTION

The present disclosure relates to a process for the production of para-xylene using a combination of a high selective toluene disproportionation process which produces a $C_8+$ stream and a crystallization process that separates the para-xylene from the $C_8+$ stream.

BACKGROUND

The $C_8$ alkylbenzenes, ethylbenzene (EB), para-xylene (PX), ortho-xylene (OX) and meta-xylene (MX) are often present together in a typical industrial $C_8$ aromatic product stream from a chemical plant or a refinery. For instance, commercially available PxMax, Mobil Selective Toluene Disproportionation and Mobil Toluene Disproportionation processes may produce such a stream.

Of the three xylene isomers, PX has the largest commercial market. PX is used primarily for manufacturing purified terephthalic acid (PTA) and terephthalate esters such as dimethyl terephthalate (DMT), which are used for making various polymers such as poly(ethylene terephthalate), or PET, poly(propylene terephthalate), or PPT, and poly(butene terephthalate), or PBT. Different grades of PET are used for many different popular consumer goods such as films, synthetic fibers, and plastic bottles for soft drinks. PPT and PBT may be used for making similar products with different properties.

Fractional distillation is a commonly used method for many processes in many industrial plants to separate chemicals. However, it is often difficult to use such a conventional fractional distillation technology to separate the EB and different xylene isomers efficiently and economically because the boiling points of the four $C_8$ aromatics fall within a very narrow 8° C. range, from about 136° C. to about 144° C. (see Table 1). The boiling points of PX and EB are about 2° C. apart. The boiling points of PX and MX are only about 1° C. apart. As a result, large equipment, significant energy consumption, and/or substantial recycles would be required to provide effective and satisfactory xylene separations.

TABLE 1

| $C_8$ compound | Boiling Point (° C.) | Freezing Point (° C.) |
| --- | --- | --- |
| EB | 136 | −95 |
| PX | 138 | 13 |
| MX | 139 | −48 |
| OX | 144 | −25 |

Fractional crystallization in a crystallizer takes advantage of the differences between the freezing points and solubilities of the $C_8$ aromatic components at different temperatures. Due to its higher freezing point, PX is usually separated as a solid in such a process while the other components are recovered in a PX-depleted filtrate. High PX purity, a key property needed for satisfactory commercial conversion of PX to PTA and/or DMT in most plants, can be obtained by this type of fractional crystallization. U.S. Pat. No. 4,120,911 provides a description of this method. A crystallizer that may operate in this manner is described in U.S. Pat. No. 3,662,013. Commercially available processes and crystallizers include the crystallization isofining process, the continuous countercurrent crystallization process, the direct contact $CO_2$ crystallizer, and the scraped drum crystallizer. Due to high utility usage and the formation of a eutectic between PX and MX, it is usually more advantageous to use a feed with as high an initial PX concentration as possible when using fractional crystallization to recover PX.

The term "shape-selective catalysis" describes unexpected catalytic selectivities in zeolites. The principles behind shape selective catalysis have been reviewed extensively, e.g., by N. Y. Chen, W. E. Garwood and F. G. Dwyer, "Shape Selective Catalysis in Industrial Applications," 36, Marcel Dekker, Inc. (1989). Within a zeolite pore, hydrocarbon conversion reactions such as paraffin isomerization, olefin skeletal or double bond isomerization, oligomerization and aromatic disproportionation, alkylation or transalkylation reactions are governed by constraints imposed by the channel size. Reactant selectivity occurs when a fraction of a feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective toluene disproportionation to p-xylene.

The production of PX is typically performed by toluene disproportionation over a catalyst under conversion conditions. Examples include the toluene disproportionation, as described by Pines in "The Chemistry of Catalytic Hydrocarbon Conversions", Academic Press, N.Y., 1981, p. 72. Such methods typically result in the production of a mixture including PX, OX, and MX. Depending upon the degree of selectivity of the catalyst for PX (para-selectivity) and the reaction conditions, different percentages of PX are obtained. The yield, i.e., the amount of xylene produced as a proportion of the feedstock, is also affected by the catalyst and the reaction conditions.

The equilibrium reaction for the conversion of toluene to xylene and benzene products normally yields about 24% PX, about 54% MX, and about 22% OX among xylenes.

Conventionally, PX production by toluene disproportionation comprises:
  a) toluene disproportionation step to produce a product stream having $C_7-$ hydrocarbons including benzene and toluene, $C_8$ hydrocarbons including PX, MX, OX, and ethylbenzene, and $C_9+$ hydrocarbons;
  b) a separation system comprising:
    1. a $C_7-$ separation step to separate the $C_7-$ hydrocarbons from the product stream to form a $C_7-$ depleted stream; and a $C_9+$ separation step to separate the $C_9+$ hydrocarbons from the $C_7-$ depleted stream to form a $C_7-$ and $C_9+$ depleted stream which is enriched with $C_8$ hydrocarbons as comparing with the product stream; or
    2. a $C_9+$ separation step to separate the $C_9+$ hydrocarbons from the product stream to form a $C_9+$ depleted stream; and a $C_7-$ separation step to separate the $C_7-$ hydrocarbons from the $C_9+$ depleted stream to form a C7− and C9+ depleted stream which is enriched with C8 hydrocarbons as comparing with the product stream; or 3. a C7− and C9+ separation step to separate C7− and C9+ hydrocarbons from the product stream to form a C7− and C9+ depleted stream which is enriched with C8 hydrocarbons as comparing with the product stream; and c) a PX separation step to separate PX from at least a portion of the C7− and C9+ depleted stream.

Conveniently, the PX separation step (c) normally comprises a crystallization step to produce a PX product with desired purity, e.g., at least 99 wt %. At least a portion of the C7− and C9+ depleted stream is used as a feedstock for the PX separation step (c). Depending on the desired purity of the PX product and depending on the PX concentration in the C7− and C9+ depleted stream, a multi-stage crystallization unit or a multi-stage adsorption unit may be needed.

Crystallization methods can be used to separate PX (p-xylene) from a C8 aromatic starting material which contains ethylbenzene, as well as the three xylene isomers. PX has a freezing point of 13.3° C., MX has a freezing point of −47.9° C. and OX has a freezing point of −25.2° C. However, conventional crystallization methods can be used to make PX with a purity of over 99.5 wt. % only with great expense.

Crystallization processes to recover PX from a mixture of C8 aromatics requires cooling the feed mixture. Because its melting point is much higher than that of the other C8 aromatics, PX is readily separated in the crystallizer after refrigeration of the stream. In conventional PX crystallization processes, the feed contains about 22 to about 23 wt. % PX. This is the type of feed that is generally obtained from catalytic reforming of naphtha, xylene isomerization, and non-shape selective toluene disproportionation (TDP) processes, in which the relative proportion of xylene isomers is close to equilibrium at reaction temperatures. For the production of high purity PX (>99.5 to >99.8 wt %) from these feeds, these feeds are cooled, crystallized and separated at a very cold temperature, normally −65 to −70.5° C. In order to recover most of the PX from solution, the feeds sometimes have to be cooled to as low as about −85° to −95° F. The crystals are melted, and the resulting solution is recrystallized and separated at a warmer temperature for maximum PX purity. Because of the constraint imposed by the eutectic temperature, PX recovery from conventional crystallization processes is generally limited to about 60-65%. Therefore, these processes generally have less favorable economics compared to the newer adsorption based PX recovery technologies, which can recover 97-98% of the feed PX, and have lower capital and operating costs.

U.S. Pat. No. 5,448,005 discloses a crystallization process for PX recovery. A single temperature crystallization production stage is used for producing PX from a feed having a PX concentration above equilibrium, such as from a toluene disproportionation process. Scavenger stages are also used to raise the PX recovery rate.

U.S. Pat. No. 5,498,822 discloses a crystallization process for PX recovery. A single temperature crystallization stage is used for producing PX from a feed having an above equilibrium PX concentration, such as from toluene disproportionation.

Various methods are known in the art for increasing the para-selectivity of zeolite catalysts, for example, U.S. Pat. Nos. 5,349,113, 5,498,814, 5,349,114, 5,476,823, 5,367,099, 5,403,800, 5,365,004, 5,610,112, 5,455,213, 5,516,736, 5,495,059, 5,633,417, 5,659,098, 6,576,582 and 6,777,583.

A modified crystallization process (WO95/26946) may be used when the feed contains a relatively high concentration of PX. The C8 aromatic mixture obtained from selective toluene disproportionation (STDP) processes generally contains over 70 wt % PX. For this type of feed, high recovery of PX is possible using a single production stage at relatively high temperature, −17.8° C. to 10° C. The filtrate is processed through one or more scavenger stages operating at lower temperature, −28.9° C. to −1.1° C., to recover additional PX, which is recycled to the production stage for final purification. When the C8 aromatic mixture contains over 97% PX, it is possible to obtain over 90% recovery in a single production stage operating at −28.9° C. to 10° C., with no scavenger stage (WO95/26947). Such mixtures may be obtained from STDP processes using a silica modified catalyst.

Because of their reduced refrigeration requirements and greater potential recovery of PX, these modified crystallization processes are generally competitive with adsorption based processes. It is believed that the feedstock to the crystallization step (c) requires very low level of C9+ hydrocarbons, which may interfere with the performance of the crystallization unit. Therefore, a C9+ separation step is required to remove C9+ from the product stream of step (a), normally a C9+ distillation column is needed to achieve desired C9+ level in a feedstock for the PX separation step (c).

It has now been surprisingly found that the C9+ separation step may be eliminated or minimized by the combination of high selective toluene disproportionation process which produces a C8 stream and a crystallization process. The elimination or minimization of the C9+ separation step can reduce energy consumption, capital cost, operational cost, and emission to the environment for a PX production plant, which will translate to low PX cost of production and less emission to the local environment.

SUMMARY OF THE DISCLOSURE

In some embodiments, this disclosure relates to a process of producing PX comprising providing a C8+ feedstock, having C8 hydrocarbons and C9+ hydrocarbons, to a crystallization unit under crystallization conditions to produce a PX enriched stream having a PX concentration of at least 99.5 wt % based on the weight of the PX enriched stream, wherein the C8+ feedstock has a PX concentration of at least 70 wt % based on total weight of xylenes in the C8+ feedstock, which the C8+ feedstock having a C9+ hydrocarbons concentration in a range from 1 wppm to 10 wt % based on the total weight of the C8+ feedstock.

In other embodiments, this disclosure relates to a process of producing PX comprising: (a) providing a toluene feedstock having toluene to a reaction zone; (b) contacting the toluene with a catalyst under toluene disproportionation conditions to form an effluent having C7− hydrocarbons, C8 hydrocarbons and C9+ hydrocarbons, wherein the C8 hydrocarbons comprise PX, MX, and OX, wherein the effluent has a PX concentration of at least 70 wt % based on total weight of xylenes in the effluent; (c) separating at least a portion of C7− hydrocarbons from the effluent to from a C8+ feedstock, wherein the C8+ feedstock has a C9+ hydrocarbons concentration from 1 wppm to 10 wt % based on the total weight of the C8+ feedstock; and (d) supply at least a portion of the C8+ feedstock to a crystallization unit under crystallization conditions to produce a PX enriched stream having a PX concentration of at least 99.5 wt % based on the weight of the PX enriched stream.

In some aspects of this disclosure, the feedstock supplied to the crystallization unit is made by a STDP process consisting essentially of:

(a) a toluene purifying step to produce a toluene feedstock comprising at least 90 wt. % toluene and non-aromatic hydrocarbons ranging from 1 to 10 wt % based on the weight of the toluene feedstock; wherein the toluene purifying step has feed(s) comprises an aromatic product stream from a catalytic reformer, an aromatic product stream from a catalytic cracker, and/or an aromatic product stream from a steam cracker, wherein the aromatic product stream from a catalytic reformer, the aromatic product stream from a catalytic cracker, or the aromatic product stream from a steam cracker comprises at least 1 wppm to about 15 wt % non-aromatic hydrocarbons;

(b) contacting the toluene feedstock with a catalyst under toluene disproportionation conditions to product a toluene disproportionation product having light gases, Bz, PX, MX, OX, $C_9+$ and unreacted toluene, wherein the toluene disproportionating step has a toluene conversion ranging from about 15 to 35 wt % based on the toluene in the toluene feedstock, and wherein the toluene disproportionation product has a PX concentration of at least 70 wt % based on total xylenes in the toluene disproportionation product; and (c) separating at least a portion of the light gases, at least a portion of the Bz, and at least a portion of the unreacted toluene from the toluene disproportionation product to produce the feedstock of any one of claims 1, 2, 3, 5, 6, and 7.

In some embodiments, this disclosure relates to a process of producing PX consisting essentially of:

(a) a toluene purifying step to produce a toluene feedstock comprising at least 90 wt. % toluene and non-aromatic hydrocarbons ranging from 1 to 10 wt % based on the weight of the toluene feedstock; wherein the toluene purifying step has feed(s) comprises an aromatic product stream from a catalytic reformer, an aromatic product stream from a catalytic cracker, and/or an aromatic product stream from a steam cracker, wherein the aromatic product stream from a catalytic reformer, the aromatic product stream from a catalytic cracker, or the aromatic product stream from a steam cracker comprises at least 1 wppm to about 15 wt % non-aromatic hydrocarbons;

(b) contacting the toluene feedstock with a catalyst under toluene disproportionation conditions to product a toluene disproportionation product having light gases, Bz, PX, MX, OX, $C_9+$ and unreacted toluene, wherein the toluene disproportionating step has a toluene conversion ranging from about 15 to 35 wt % based on the toluene in the toluene feedstock, and wherein the toluene disproportionation product has a PX concentration of at least 70 wt % based on total xylenes in the toluene disproportionation product;

(c) separating at least a portion of the light gases, at least a portion of the Bz, and at least a portion of the unreacted toluene from the toluene disproportionation product to produce a $C_8+$ feedstock; and (d) providing the $C_8+$ feedstock to a crystallization unit under crystallization conditions to produce a PX enriched stream having a PX concentration of at least 99.7 wt % based on the weight of the PX enriched stream, wherein the $C_8+$ feedstock has a PX concentration of at least 70 wt % based on total weight of xylenes in the $C_8+$ feedstock, which the $C_8+$ feedstock having a $C_9+$ hydrocarbons concentration in a range from 5000 wppm to 10 wt % based on the total weight of the $C_8+$ feedstock.

In additional embodiments, this disclosure relates to an apparatus for producing a PX rich stream, which comprises: (a) a reactor having an inlet and an outlet; (b) a separation unit having an inlet and a first outlet and a second outlet, the inlet of the separation unit being fluidicly connected to the outlet of the reactor; and (c) a crystallization unit having an inlet, a first outlet, and a second outlet, the inlet of the crystallization unit being fluidicly connected to the second outlet of the separation unit.

DETAILED DESCRIPTION

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "wppm" as used herein is defined as parts per million by weight.

All weights of molecular sieve, weights of binder, and weights of catalyst composition, as used in herein, are based on the calcined weight (i.e., calcined at 510° C. in air for at least one hour).

The term "$C_n$" hydrocarbon wherein n is an positive integer, e.g., 1, 2, 3, 4, 5, 6, 7, 8, 9, 10, 11, 12, as used herein means a hydrocarbon having n number of carbon atom(s) per molecular. For example, $C_n$ aromatics means an aromatic hydrocarbon having n number of carbon atom(s) per molecular; $C_n$ paraffin means a paraffin hydrocarbon having n number of carbon atom(s) per molecular; $C_n$ olefin means an olefin hydrocarbon having n number of carbon atom(s) per molecular. The term "$C_n+$" hydrocarbon wherein n is an positive integer, e.g., 1, 2, 3, 4, 5, 6, 7, 8, 9, 10, 11, 12, as used herein means a hydrocarbon having at least n number of carbon atom(s) per molecular. The term "$C_n-$" hydrocarbon wherein n is an positive integer, e.g., 1, 2, 3, 4, 5, 6, 7, 8, 9, 10, 11, 12, as used herein means a hydrocarbon having no more than n number of carbon atom(s) per molecular.

The term "$C_n+$" feedstock, wherein n is an positive integer, e.g., 1, 2, 3, 4, 5, 6, 7, 8, 9, 10, 11, 12, as used herein means a feedstock comprising a majority (greater than 50 wt % based on the total weight of the feedstock) hydrocarbons having at least n number of carbon atom(s) per molecular. The term "$C_n-$" feedstock wherein n is an positive integer, e.g., 1, 2, 3, 4, 5, 6, 7, 8, 9, 10, 11, 12, as used herein means a feedstock comprising a majority (greater than 50 wt % based on the total weight of the feedstock) hydrocarbons having no more than n number of carbon atom(s) per molecular.

In some embodiments, this disclosure relates to a process of producing PX comprising providing a $C_8+$ feedstock, having $C_8$ hydrocarbons and $C_9+$ hydrocarbons, to a crystallization unit under crystallization conditions to produce a PX enriched stream having a PX concentration of at least 99.5 wt % based on the weight of the PX enriched stream, wherein the $C_8+$ feedstock has a PX concentration of at least 70 wt % based on total weight of xylenes in the $C_8+$ feedstock, which the $C_8+$ feedstock having a $C_9+$ hydrocarbons concentration in a range from 1 wppm to 10 wt % based on the total weight of the $C_8+$ feedstock.

The term "non-aromatic" hydrocarbon means a hydrocarbon having no aromatic ring. Examples of non-aromatic hydrocarbon are paraffin(s), olefin(s), cyclic paraffin(s), or cyclic olefin(s).

In other embodiments, this disclosure relates to a process of producing PX comprising: (a) providing a toluene feedstock having toluene to a reaction zone; (b) contacting the toluene with a catalyst under toluene disproportionation conditions to form an effluent having $C_7-$ hydrocarbons, $C_8$ hydrocarbons and $C_9+$ hydrocarbons, wherein the $C_8$ hydrocarbons comprise PX, MX, and OX, wherein the effluent has a PX concentration of at least 70 wt % based on total weight of xylenes in the effluent; (c) separating at least a portion of $C_7-$ hydrocarbons from the effluent to from a $C_8+$ feedstock, wherein the $C_8+$ feedstock has a $C_9+$ hydrocarbons concentration from 1 wppm to 10 wt % based on the total weight of the $C_8+$ feedstock; and (d) supply at least a portion of the $C_8+$ feedstock to a crystallization unit under crystallization conditions to produce a PX enriched stream having a PX concentration of at least 99.5 wt % based on the weight of the PX enriched stream.

$C_8+$ Feedstock

The $C_8+$ feedstock useful for this disclosure has $C_8$ hydrocarbons and $C_9+$ hydrocarbons. In some embodiment, a $C_8+$ feedstock useful for this disclosure is produced by separation/purification from a hydrocarbon stream made in a reforming process, a hydrocracking process, a toluene disproportionation process, a selective toluene disproportionation process, a toluene methylation process, or any combination thereof. The $C_8+$ feedstock useful for this disclosure has a PX concentration of at least 70 wt % based on total weight of xylenes in the $C_8+$ feedstock and the $C_8+$ feedstock has a $C_9+$ hydrocarbons concentration in a range from 1 wppm to 10 wt % based on the total weight of the $C_8+$ feedstock The following PX concentration, in wt % based on total weight of xylenes in a $C_8+$ feedstock, are useful lower PX concentration limits for all disclosure processes: 70, 75, 80, 85, 89, 93, and 95. The following PX concentration, in wt % based on total weight of xylenes in the $C_8+$ feedstock, are useful upper PX concentration limits for all disclosure processes: 99, 98, 97, 96, 95, and 90. The PX concentration, in wt % based on total weight of xylenes in the $C_8+$ feedstock may be present in an amount ranging from 70 wt % to 99 wt % in one embodiment, alternatively 75 wt % to 98 wt %, alternatively from 80 wt % to 97 wt %, alternatively 85 to 95 wt %, alternatively 85 wt % to 99 wt %, alternatively and from 85 wt % to 95 wt % in another embodiment.

The following $C_9+$ hydrocarbons concentration, based on the total weight of the $C_8+$ feedstock, are useful lower $C_9+$ hydrocarbons concentration limits for all disclosure processes: 1 wppm, 2 wppm, 5 wppm, 10 wppm, 50 wppm, 100 wppm, 200 wppm, 500 wppm, 1000 wppm, 2000 wppm, 5000 wppm, 1 wt %, 2 wt % and 5 wt %. The following $C_9+$ hydrocarbons concentration, based on the total weight of the $C_8+$ feedstock, are useful upper $C_9+$ hydrocarbons concentration limits for all disclosure processes: 100 wppm, 200 wppm, 500 wppm, 1000 wppm, 2000 wppm, 5000 wppm, 1 wt %, 2 wt %, 5 wt % and 10 wt %. The $C_9+$ hydrocarbons concentration, based on the total weight of the $C_8+$ feedstock may be present in an amount ranging from 1 wppm to 10 wt % in one embodiment, alternatively 10 wppm to 5 wt %, alternatively from 20 wppm to 2 wt %, alternatively 1 wppm to 1 wt %, alternatively 2 wppm to 1 wt %, alternatively and from 5 wppm to 1 wt % in another embodiment.

In some embodiments, the $C_8+$ feedstock may further comprise naphthalene. When naphthalene is present in the $C_8+$ feedstock, the naphthalene concentration, in mol %, based on the PX free $C_8+$ in the $C_8+$ feedstock is ranging from about 0.0001 to 10 mol %. The following naphthalene concentration, in mol %, based on the PX free $C_8+$ hydrocarbons in a $C_8+$ feedstock, are useful lower naphthalene concentration limits for all disclosure processes: 0.0001, 0.0002, 0.0005, 0.001, 0.005, 0.01, 0.02, 0.05, 0.1, 0.2, 0.5, 1 mol %, 2 mol % and 5 mol %. The following naphthalene concentration, based on the PX free $C_8+$ in the $C_8+$ feedstock, are useful upper naphthalene concentration limits for all disclosure processes: 0.01, 0.02, 0.05, 0.1, 0.2, 0.5, 1 mol %, 2 mol %, 5 mol % and 10 mol %. The naphthalene concentration based on the PX free $C_8+$ hydrocarbons in a $C_8+$ feedstock may be present in an amount ranging from 0.0001 to 10 mol % in one embodiment, alternatively 0.001 to 5 mol %, alternatively from 0.002 to 2 mol %, alternatively 0.0001 to 1 mol %, alternatively 0.0002 to 1 mol %, alternatively and from 0.0005 to 1 mol % in another embodiment. The naphthalene concentration, in mol %, based on the PX free $C_8+$ hydrocarbons in a $C_8+$ feedstock is calculated with the following equation:

$$\text{naphthalene concentration} = \frac{\text{total mole of the naphthalene in the } C_8+\text{ feedstock} \times 100}{\text{Mole of } C_8+\text{ hydrocarbons in the } C_8+\text{ feedstock} - \text{Mole of } PX \text{ in the } C_8+\text{ feedstock}}$$

PX Enriched Stream Product

In one embodiment, the PX enriched stream produced by the crystallization unit has a PX concentration of at least 99.5 wt % based on the weight of the PX enriched stream. The following PX concentration of the PX enriched stream, in wt %, based on the weight of the PX enriched stream, are useful lower PX concentration limits for all disclosure processes: 95, 96, 97, 98, 99, 99.5, 99.6, 99.7, 99.8, 99.85, 99.86, 99.87, 99.88 and 99.9. The following PX concentration of the PX enriched stream, in wt %, based on the weight of the PX enriched stream, are useful upper PX concentration limits for all disclosure processes: 99.8, 99.85, 99.86, 99.87, 99.88, 99.89, 99.9, 99.95 and 99.999999. The following PX concentration of the PX enriched stream, in wt %, based on the weight of the PX enriched stream, may be present in an amount ranging from 95 to 100 in one embodiment, alternatively 98 to 9.99, alternatively from 99 to 99.99, alternatively 99.5 to 99.99, alternatively 99.6 to 99.99, alternatively and from 99.7 to 99.99 in another embodiment.

Crystallization Conditions

In some embodiments, the crystallization unit is normally operated at a temperature of at least 1° C. higher than the highest eutectic point of PX with MX, PX with naphthalene (when naphthalene is present in the $C_8+$ feedstock) or PX with other $C_8+$ hydrocarbons. In other embodiments, the crystallization unit is operated at a temperature of at least 2° C., 3° C., 4° C., 5° C., 6° C., 7° C., 8° C., 9° C., 10° C., 15° C., or 20° C. higher than the point of PX with MX, PX with naphthalene (when naphthalene is present in the $C_8+$ feedstock) or PX with other $C_8+$ hydrocarbons. In other embodiments, the crystallization unit is operated at a temperature of no more than 100° C., 50° C., 40° C., 30° C., or 20° C. higher than the highest eutectic point of PX with MX, PX with naphthalene (when naphthalene is present in the $C_8+$ feedstock) or PX with other $C_8+$ hydrocarbons. In some embodiments, the crystallization unit is operated at a temperature ranging from 1° C. to 100° C., alternatively, 2° C. to 50° C., alternatively, 5° C. to 50° C., alternatively, 5° C. to 30° C., or alternatively, 5° C. to 20° C.

In a preferred embodiment, the crystallization unit is operated at a temperature of at least −30° C., alternatively −25° C., alternatively −20° C., alternatively −18° C., alternatively −15° C., alternatively −10° C., alternatively −5° C., alternatively 0° C., alternatively 5° C., or alternatively 10° C.

In some embodiments, when the $C_8+$ feedstock having a PX concentration of greater than 70 wt % based on the total xylenes in the $C_8+$ feedstock, the crystallization unit is operated using a single production stage at relatively high temperature, −17.8° C. to 10° C., wherein the filtrate is processed through one or more scavenger stages operating at lower temperature, −28.9° C. to −1.1° C., to recover additional PX, which is recycled to the production stage for final purification as disclosed in WO95/26946. Alternatively, when the $C_8+$ feedstock having a PX concentration of greater than 97 wt % based on the total xylenes in the $C_8+$ feedstock, the crystallization unit may be operated using a single production stage operating at −28.9° C. to 10° C., with no scavenger stage as disclosed in WO95/26947. The entirety of WO95/26946 and WO95/26947 are incorporated by reference.

The temperatures referenced above pertain to the coldest crystallizer stage. In practice, it is known that two or three stages at a range of temperatures are needed to obtain an acceptably high purity PX product. However, the temperature of the coldest stage is significant because it determines the maximum PX recovery that may be obtained.

PX depleted filtrate is recycled to each stage to control the solids content of the crystallizer effluent that is sent to the liquid-solid separation apparatus, normally a centrifuge. The final crystalline product is washed with a liquid, preferably high purity PX product, to displace the residual filtrate from the wet cake.

In some embodiments, the crystallization unit is operated with a PX recovery of at least 65 wt %. The following PX recovery, in wt %, based on the PX in $C_8+$ feedstock, are useful lower PX recovery limits for all disclosure processes: 70, 75, 80, 85, 90, 91, 92, 93, 94, 95, 96, 97, 98 and 99. The following PX recovery, in wt %, based on the weight of the PX in the $C_8+$ feedstock, are useful upper PX recovery limits for all disclosure processes: 75, 80, 85, 90, 91, 92, 93, 94, 95, 96, 97, 98, 99 and 99.99. The following PX recovery, in wt %, based on the weight of the PX in the $C_8+$ feedstock, may be present in an amount ranging from 95 to 100 in one embodiment, alternatively 70 to 99.9, alternatively from 80 to 99, alternatively 85 to 99.99, alternatively 90 to 99.99, alternatively and from 95 to 99.99 in another embodiment.

Selective Toluene Disproportionation

STDP provides a process for obtaining p-xylene at toluene conversions of at least 10 wt %, preferably at least about 15-25 wt %, with a PX selectivity of greater than 85 wt %, preferably at least 90 wt % based on the total xylenes in the product.

The toluene feedstock may be produced by any separation technique, such as, distillation of a feed containing toluene. Examples of a feed containing toluene are an aromatic product stream of a catalytic reformer, an aromatic product stream of a catalytic cracker, an aromatic product stream of a steam cracker, or any combination thereof. In some aspects, the aromatic product stream of a catalytic reformer, the aromatic product stream of a catalytic cracker, or the aromatic product stream of a steam cracker may optionally subject to extraction to remove non-aromatic hydrocarbons from said aromatic product stream(s). In other aspects, the aromatic product stream of a catalytic reformer, the aromatic product stream of a catalytic cracker, or the aromatic product stream of a steam cracker may not subject to extraction process without removing non-aromatic hydrocarbons from said aromatic product stream(s). The non-aromatic hydrocarbons content in the toluene feedstock is a function of the feed composition and separation technique/efficiency used to produce the toluene feedstock.

The toluene feedstock preferably includes about 50 wt % to 100 wt % toluene, more preferably at least about 80 wt % toluene based on the total weight of the toluene feedstock. Other compounds such as benzene, xylenes, trimethylbenzene, and non-aromatics may also be present in the toluene feedstock without adversely affecting the present disclosure. The amount of the non-aromatics may be in a range from about 1 wppm to 15 wt % based on the total weight of the toluene feedstock. The following non-aromatics, in wt %, based on the total weight of the toluene feedstock, are useful lower non-aromatics limits for all disclosure processes: 0.01, 0.1, 0.2, 0.5, 1, 2, 3, 4, 5, 6, 7, 8, 9, 10, 11, 12, 13 and 14. The following non-aromatics, in wt %, based on the total weight of the toluene feedstock, are useful higher non-aromatics limits for all disclosure processes: 1, 2, 3, 4, 5, 6, 7, 8, 9, 10, 11, 12, 13, 14 and 15. The following non-aromatics, in wt %, based on the total weight of the toluene feedstock, may be present in an amount ranging from 0.1 to 15 in one embodiment, alternatively 1 to 10, alternatively from 3 to 15, alternatively 3 to 10, alternatively 4 to 15, alternatively and from 4 to 10 in another embodiment.

The toluene feedstock may also be dried, if desired, in a manner which will minimize moisture entering the reaction zone. Numerous methods known in the art are suitable for drying the toluene charge for the process of the disclosure. These methods include percolation through any suitable desiccant, for example, silica gel, activated alumina, molecular sieves or other suitable substances, stripping, distillation, and/or the use of liquid charge dryers.

The catalytic molecular sieves useful in accordance with the methods of the present disclosure are preferably in the hydrogen form prior to modification, but may be in the ammonium or sodium form. Preferably, the catalytic molecular sieve comprises an intermediate pore-size molecular sieve such as a ZSM-5, ZSM-11, ZSM-22, ZSM-23, or ZSM-35 as discussed above. The catalytic molecular sieves also preferably have a Constraint Index of about 1-12. The details of the method by which Constraint Index is determined are described fully in U.S. Pat. No. 4,016,218, incorporated herein by reference.

The crystal size of molecular sieves used herein is preferably greater than 0.1 micron. The accurate measurement of crystal size of molecular sieve materials is frequently very difficult. Microscopy methods, such SEM and TEM, are often used, but these methods require measurements on a large number of crystals and for each crystal measured, values may be required in up to three dimensions. For ZSM-5 materials described in the examples below, estimates were made of the effective average crystal size by measuring the rate of sorption of 2,2-dimethylbutane at 90° C. and 8 kPa-a hydrocarbon pressure. The crystal size is computed by applying the diffusion equation given by J. Crank, "The Mathematics of Diffusion" Oxford at the Clarendon Press, 1957, pp 52-56, for the rate of sorbate uptake by a solid whose diffusion properties can be approximated by a plane sheet model. In addition, the diffusion constant of 2,2-dimethylbutane, D, under these conditions is taken to be $1.5 \times 10^{-14}$ $cm^2$/sec.

The catalyst for STDP may be a catalyst selectivated by coke, silicon, metal(s), or any combination thereof.

Operating conditions employed in the process of the present disclosure will affect the para-selectivity and toluene conversion. Such conditions include the temperature, pressure, space velocity, molar ratio of the reactants, and the hydrogen to hydrocarbon mole ratio ($H_2$/HC). It has also been observed that an increased space velocity (WHSV) can enhance the para-selectivity of the modified catalyst in alkylbenzene disproportionation reactions. This characteristic of the modified catalyst allows for substantially improved throughput when compared to current commercial practices. In addition, it has been observed that the disproportionation process may be performed using $H_2$ as a diluent, thereby dramatically increasing the cycle length of the catalyst. For example, it has been observed that an increase in temperature can increase the activity of the modified catalyst.

A selectivated and steamed catalytic molecular sieve may be contacted with a toluene feedstock under conditions for effecting vapor-phase disproportionation. Conditions effective for accomplishing the high para-selectivity and acceptable toluene disproportionation conversion rates include a reactor inlet temperature of from about 200° C. to about 600° C., preferably from 350° C. to about 540° C.; a pressure of from about 101.3 kPa-a to about 34.48 MPa-a, preferably from about 689 kPa-a to about 6.89 MPa-a; a WHSV of from about 0.1 to about 20 $hr^{-1}$, preferably from about 2 to about 10 $hr^{-1}$; and a $H_2$/HC mole ratio of from about 0.1 to about 20, preferably from about 2 to about 6. This process may be conducted in either batch or fluid bed operation, with the attendant benefits of either operation readily obtainable. The effluent may be separated and distilled to remove the desired product, i.e., p-xylene, as well as other by-products. Alternatively, the $C_8$ fraction may be subjected to further separation, as in the case of xylenes, subjected to crystallization process to yield p-xylene.

The catalyst may be further modified in order to reduce the amount of undesirable by-products, particularly ethylbenzene. The state of the art is such that the reactor effluent from standard toluene disproportionation typically contains about 0.5% ethylbenzene by-product. Upon distillation of the reaction products, the level of ethylbenzene in the $C_8$ fraction often increases to between about 3% and 4%. This level of ethylbenzene is unacceptable for polymer grade p-xylene, since ethylbenzene in the p-xylene product, if not removed, degrades the quality of fibers ultimately produced from the p-xylene product. Consequently, ethylbenzene content of the p-xylene product must be kept low. The specification for the allowable amount of ethylbenzene in the p-xylene product has been determined by the industry to be less than 0.3%. Ethylbenzene can be substantially removed by crystallization or by superfractionation processes.

In order to avoid the need for downstream ethylbenzene removal, the level of ethylbenzene by-product is advantageously reduced by incorporating a hydrogenation/dehydrogenation function within the catalyst, such as by addition of a metal compound or metal compound(s), such as platinum or platinum/tin. While platinum is the preferred metal, other metals of Groups 6 to 12 of the Periodic Table such as palladium, nickel, copper, cobalt, molybdenum, rhodium, ruthenium, silver, gold, mercury, osmium, iron, zinc, cadmium, and mixtures thereof, may be utilized. The metal may be added by cation exchange, in amounts of from about 0.001 wt % to about 2 wt %, typically about 0.5 wt %. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. The catalyst can then be filtered, washed with water and calcined at temperatures of from about 250° C. to about 500° C. It will be appreciated by those skilled in the art that similar considerations apply to processes involving alkylbenzenes other than toluene.

Apparatus for PX Production

In additional embodiments, this disclosure relates to an apparatus for producing a PX rich stream, which comprises: (a) a reactor having an inlet and an outlet; (b) a separation unit having an inlet and a first outlet and a second outlet, the inlet of the separation unit being fluidicly connected to the outlet of the reactor; and (c) a crystallization unit having an inlet, a first outlet, and a second outlet, the inlet of the crystallization unit being fluidicly connected to the second outlet of the separation unit.

A typical toluene disproportionation process comprises a toluene disproportionation reactor. Toluene feedstock is fed to the toluene disproportionation reactor optionally co-fed with $H_2$. The product normally comprises $H_2$, $C_7-$ hydrocarbons (including benzene), $C_8$ hydrocarbons (including PX, MX, and OX), and $C_9+$ hydrocarbons. The product stream is conveniently supplied to a series of fractionation units to separate $H_2$ which may be recycled to the toluene disproportionation reactor, light gases, benzene as one final product, and toluene which may recycle back to the toluene disproportionation reactor. The rest of the product after separation of $H_2$, light gases, benzene and toluene, namely $C_8+$ product stream, contains mainly xylenes and $C_9+$ hydrocarbons. Conveniently, the $C_9+$ is separated from the xylenes before further separation of PX at a crystallization unit.

In some embodiments of this disclosure, the $C_8+$ product stream is fed to a crystallizer without the $C_9+$ separation step. By eliminating the $C_9+$ separation step, e.g., eliminating a distillation tower for separating xylenes from $C_9+$, huge energy saving may be achieved. To achieve the same level of PX recovery in the downstream PX crystallizer, the crystallizer may have to be operated at a lower temperature due the presence of $C_9+$ in the $C_8+$ feedstock, which may need more energy to operate the crystallizer for the same PX recovery. For a $C_8+$ feedstock having a PX concentration of greater than 70 wt % (based on total xylenes weight in the $C_8+$ feedstock), a $C_9+$ concentration (based on the total $C_8+$ feedstock weight) of less than 10 wt %, and a naphthalene concentration (based on PX free $C_8+$ in the $C_8+$ feedstock) of less than 10 mol %, the energy saving of eliminating the $C_9+$ separation tower surprisingly outweights the extra energy needed for the crystallization unit to have equivalent PX recovery. Another advantage for the elimination of the $C_9+$ separation step is lower operating cost for operating one less separation unit, which is environmental, energy, and cost beneficial.

The following examples reflect embodiments of the disclosure and are by no means intended to be limiting of the scope of the disclosure.

EXAMPLES

A general feature for p-xylene (PX) crystallization processes is that the product recovery is a function of the feed PX concentration and the temperature of the coldest stage. The following equation for calculating recovery follows from an overall mass balance around the crystallizer:

$$R = \frac{X_F - X_E}{1 - X_E} \cdot \frac{1}{X_F} \qquad [\text{Eq. 1}]$$

where R=fractional recovery of PX;
$X_E$=equilibrium PX content of filtrate at the coldest stage; and
$X_F$=PX content of fresh feed.

Another principle of crystallizer design is that the temperature should be maintained at least 3-6° C. (5-10° F.) above the eutectic temperature to avoid contamination of the product. Therefore, the eutectic temperature sets the coldest stage temperature, which determines $X_E$ and thereby, the recovery of PX.

The following examples simulated the calculation of the eutectic temperature and potential PX recovery from the modified crystallization process based on expected composition from TDP and STDP processes.

Typical $C_8+$ fraction composition from TDP and STDP processes are listed in Table 2 and these are the basis for the simulations in examples 1-3:

TABLE 2

Typical $C_8+$ composition for TDP and STDP processes

| | Freeze Point (° C.)[1,2] | Example 1 (TDP) | Example 2 (STDP) | Example 3 (STDP) |
|---|---|---|---|---|
| | | Typical $C_8+$ composition, wt % | | |
| Ethylbenzene | −138.95 | 2.36 | 2.99 | 2.87 |
| p-Xylene | 55.86 | 23.02 | 79.24 | 85.06 |
| m-Xylene | −54.12 | 47.78 | 10.99 | 6.11 |
| o-Xylene | −13.30 | 19.83 | 1.63 | 0.93 |
| Ethyl toluene | −80.16 | 2.71 | 3.30 | 2.12 |
| Trimethylbenzenes | −13.62 | 2.28 | 0.20 | 0.12 |
| Indane | −60.54 | 0.13 | 0.06 | 0.12 |
| Propylbenzenes | −140.81 | 0.04 | 0.00 | 0.06 |
| Naphthalene | 176.52 | 0.59 | 0.71 | 1.50 |
| Durene[3] | 174.63 | 0.00 | 0.00 | 0.00 |
| Other $C_{10}$ benzenes | 20.75 | 0.03 | 0.00 | 0.12 |
| Methylnaphthalenes | 94.24 | 1.17 | 0.53 | 0.68 |
| Other $C_{11}+$ Aromatics[4] | 156.56 | 0.06 | 0.35 | 0.31 |
| | | Concentration in PX-free filtrate, mol % | | |
| Naphthalene[5] | 176.52 | 0.64 | 2.94 | 8.81 |

[1] From "Technical Data Book - Petroleum Refining", API, 5th Edition, May 1992.
[2] The highest freeze point is listed for compound classes having multiple isomers.
[3] 1,2,4,5-Tetramethyl benzene.
[4] Freeze point is listed for biphenyl.
[5] Naphthalene mol percentage on PX free basis is calculated based on total mole of naphthalene divided by the total mole of $C_8+$ in the feed without PX, i.e., Mol % Naphthalene in PX-free $C_8+$ fraction = mol % of naphthalene in $C_8+/(1 −$ mol fraction PX in $C_8+$).

For purpose of simplicity, we assume that the $C_9+$ removal step removes all $C_9+$ in the $C_8+$ fraction. The typical $C_8+$ fraction composition from TDP and STDP processes after $C_9+$ removal are renormalized to 100% and are listed in Table 3 and these are the basis for the simulations in examples 1-3:

TABLE 3

Typical $C_8+$ composition for TDP and STDP processes after $C_9+$ removal

| | Freeze Point (° C.) | Example 1 (TDP) | Example 2 (STDP) | Example 3 (STDP) |
|---|---|---|---|---|
| | | Typical $C_8+$ composition, wt % | | |
| Ethylbenzene | −138.95 | 2.54 | 3.15 | 3.02 |
| p-Xylene | 55.86 | 24.76 | 83.54 | 89.57 |
| m-Xylene | −54.12 | 51.38 | 11.59 | 6.43 |
| o-Xylene | −13.30 | 21.32 | 1.72 | 0.98 |
| Ethyl toluene | −80.16 | 0 | 0 | 0 |
| Trimethylbenzenes | −13.62 | 0 | 0 | 0 |
| Indane | −60.54 | 0 | 0 | 0 |
| Propylbenzenes | −140.81 | 0 | 0 | 0 |
| Naphthalene | 176.52 | 0 | 0 | 0 |
| Durene | 174.63 | 0 | 0 | 0 |
| Other $C_{10}$ benzenes | 20.75 | 0 | 0 | 0 |

TABLE 3-continued

Typical $C_8+$ composition for TDP and STDP processes after $C_9+$ removal

| | Freeze Point (° C.) | Example 1 (TDP) | Example 2 (STDP) | Example 3 (STDP) |
|---|---|---|---|---|
| | | Typical $C_8+$ composition, wt % | | |
| Methylnaphthalenes | 94.24 | 0 | 0 | 0 |
| Other $C_{11}+$ Aromatics | 156.56 | 0 | 0 | 0 |

For the $C_8$ fractions, the eutectic point of interest is the temperature where m-xylene (MX) co-crystallizes with PX. For the $C_8+$ fraction, the mixture contains small concentrations of other components which have freezing points above PX. These mixtures generally exhibit near-ideal solution behavior in which the freezing point depression of each component is dependent on its pure component properties and mole fraction. Therefore, even though a component has a higher freezing point than PX, it will not necessarily crystallize before PX, depending on its mole fraction in the mixture. In the examples, the limiting eutectic point for each mixture was determined using a modified version of the van't Hoff equation:

$$\ln(X_i) = -A(T^*-T)[1+B(T^*-T)] \quad [Eqn\ 2]$$

where
$X_i$=liquid phase mol fraction of component i at equilibrium
$T^*$=freezing point of the pure component, ° K
$T$=mixture temperature, ° K $$A = \frac{\Delta H^*}{R(T^*)^2},$$

a cryoscopic constant, ° K⁻

$$B = \frac{1}{T^*} - \frac{\Delta C_P}{2\Delta H^*},$$

a cryoscopic constant, ° K⁻¹
$\Delta H^*$=molar heat of fusion at T*, kcal/mol
$\Delta C_P$=difference in molar heat capacity of liquid and solid, kcal/mol-° K
R=gas constant, 1.9872 kcal/mol-° K Equation 2 is applicable for ideal solutions, such as the $C_8+$ hydrocarbon fractions considered in these examples. It differs from the simple van't Hoff equation by including a correction for the variation in enthalpy of fusion with temperature. It is therefore more accurate when there is a significant depression of the freezing point. Values of the cryoscopic constants A and B for the components of interest are given in Table 4:

TABLE 4

Cryoscopic constants A and B for PX, MX, OX, EB, and naphthalene

| Component | A, ° K⁻¹ | B, ° K⁻¹ |
|---|---|---|
| p-xylene | 0.02509 | 0.0028 |
| o-xylene | 0.02660 | 0.0030 |
| m-xylene | 0.02742 | 0.0027 |
| ethylbenzene | 0.03479 | 0.0029 |
| naphthalene | 0.01830 | 0.0027 |

Then the concentration of PX at least 5° C. above the eutectic was used to determine the potential recovery by equation 1.

Example 1

With the $C_9+$ removal tower (conveniently also called $C_8$ tower), the simulation shown that the MX eutectic point was limited at a temperature of −64.3° C. Allowing for the 5° C. margin above the eutectic, the cold stage operating temperature is −59.3° C. At this temperature, estimated recovery for 24.8 wt % PX feed was 61.7%.

Without the $C_9+$ removal tower, the simulation shown that the MX eutectic point was limited at a temperature of −67.2° C. For the same recovery as the case with a $C_9+$ removal tower, the simulation shown that the required cold stage operating temperature was −61.3° C. Refrigeration demands increase slightly in this case compared to operation with the $C_9+$ removal tower. However, the increased cost of refrigeration is more than offset by the utility savings achieved by the elimination of the $C_9+$ removal tower.

Example 2

With the $C_9+$ removal tower, the simulation has shown that the MX eutectic point was limiting at a temperature of −63.4° C. Allowing for the 5° C. margin above the eutectic, the cold stage operating temperature is −58.4° C. At this temperature, estimated recovery for 83.5 wt % PX feed was 97.4%. Although the cold stage could potentially be operated at −58.4° C., it is advantageous in this case to design the cold stage for a higher temperature in order to eliminate the need for ethylene refrigerant. The recovery at −18° C. cold stage temperature for this case was simulated as 85.4%.

Without the $C_9+$ removal tower, the simulation has shown that the naphthalene/PX eutectic point was limited at a temperature of −63.2° C. Allowing for the 5° C. margin above the eutectic, the cold stage operating temperature is −58.2° C. At this temperature, estimated recovery for 83.5 wt % PX feed was 96.7%. In order to obtain the same recovery as the case with the $C_9+$ removal tower (85.4%), the simulated cold stage temperature was −23° C. Refrigeration demands increase in this case compared to operation with the $C_9+$ removal tower. However, the increased cost of refrigeration is more than offset by the utility savings achieved by the elimination of the $C_9+$ removal tower.

Example 3

With the $C_9+$ removal tower, the MX eutectic point is limiting at a temperature of −67.4° C. Allowing for the 5° C. margin above the eutectic, the cold stage operating temperature is −62.4° C. At this temperature, estimated recovery for 89.57 wt % PX feed was 98.7%. Although the cold stage could potentially be operated at −62.4° C., it is advantageous in this case to design the cold stage for a higher temperature in order to eliminate the need for ethylene refrigerant. The recovery at −18° C. cold stage temperature for this case was simulated as 91.4%.

Without the $C_9+$ removal tower, the simulation shown that the naphthalene/PX eutectic point was limited at a temperature of −32.1° C. Allowing for the 5° C. margin above the eutectic, the cold stage operating temperature is −27.1° C. At this temperature, estimated recovery for 89.57 wt % PX feed was 92.0%. In order to obtain the same recovery as the case with the $C_9+$ removal tower (91.4%), the simulation indicated that the cold stage temperature was reduced by 7° C. to −25° C. Refrigeration demands increase in this case compared to operation with the $C_9+$ removal tower. However, the increased cost of refrigeration is more than offset by the utility savings achieved by the elimination of the $C_9+$ removal tower.

TABLE 5

Summary of eutectic points, operating temperatures and PX recovery of examples 1-3

| | Example 1 | | Example 2 | | Example 3 | |
| --- | --- | --- | --- | --- | --- | --- |
| | Remove $C_9+$ | No $C_9+$ removal | Remove $C_9+$ | No $C_9+$ removal | Remove $C_9+$ | No $C_9+$ removal |
| Eutectic point (° C.) | −64.3 | −67.2 | −63.4 | −63.2 | −67.4 | −32.1 |
| Operating Temperature (° C.) | −59.3 | −61.3 | −58.4 | −58.2 | −62.4 | −27.1 |
| PX recovery | 61.7% | 61.7% | 97.4% | 96.7% | 98.7% | 92.0% |
| No ethylene refrigerant mode operating Temperature (° C.) | N/A | N/A | −18 | −23 | −18 | −25 |
| PX recovery for no ethylene refrigerant mode operating Temperature (° C.) | N/A | N/A | 85.4% | 85.4% | 91.4% | 91.4% |

All patents and patent applications, test procedures (such as ASTM methods), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

The meanings of terms used herein shall take their ordinary meaning in the art; reference shall be taken, in particular, to Handbook of Petroleum Refining Processes, Third Edition, Robert A. Meyers, Editor, McGraw-Hill (2004). In addition, all patents and patent applications, test procedures (such as ASTM methods), and other documents cited herein are fully incorporated by reference to the extent such disclosure is not inconsistent with this disclosure and for all jurisdictions in which such incorporation is permitted. Also, when numerical lower limits and numerical upper limits are listed herein, ranges from any lower limit to any upper limit are contemplated. Note further that Trade Names used herein are indicated by a ™ symbol or ® symbol, indicating that the names may be protected by certain trademark rights, e.g., they may be registered trademarks in various jurisdictions.

While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

In some embodiments, this disclosure relates to:

Paragraph 1. A process of producing PX comprising providing a $C_8+$ feedstock, said $C_8+$ feedstock has $C_8$ hydrocarbons and $C_9+$ hydrocarbons, to a crystallization unit under crystallization conditions to produce a PX enriched stream having a PX concentration of at least 99.5 wt % based on the weight of said PX enriched stream,
wherein said $C_8+$ feedstock has a PX concentration of at least 70 wt % based on total weight of xylenes in said $C_8+$ feedstock, which said $C_8+$ feedstock having a $C_9+$ hydrocarbons concentration in a range from 1 wppm to 10 wt % based on the total weight of said $C_8+$ feedstock.

Paragraph 2. A process of producing PX comprising:
(a) providing a toluene feedstock having toluene to a reaction zone;
(b) contacting said toluene with a catalyst under toluene disproportionation conditions to form an effluent having $C_7-$ hydrocarbons, $C_8$ hydrocarbons and $C_9+$ hydrocarbons, wherein said $C_8$ hydrocarbons comprise PX, MX, and OX, wherein said effluent has a PX concentration of at least 70 wt % based on total weight of xylenes in said effluent;
(c) separating at least a portion of $C_7-$ hydrocarbons from said effluent to from a $C_8+$ feedstock, wherein said $C_8+$ feedstock has a $C_9+$ hydrocarbons concentration from 1 wppm to 10 wt % based on the total weight of the $C_8+$ feedstock; and
(d) supply at least a portion of said $C_8+$ feedstock to a crystallization unit under crystallization conditions to produce a PX enriched stream having a PX concentration of at least 99.5 wt % based on the weight of said PX enriched stream.

Paragraph 3. A process of producing PX consisting essentially of:
(e) a toluene purifying step to produce a toluene feedstock comprising at least 90 wt. % toluene and non-aromatic hydrocarbons ranging from 1 to 10 wt % based on the weight of said toluene feedstock; wherein said toluene purifying step has feed(s) comprises an aromatic product stream from a catalytic reformer, an aromatic product stream from a catalytic cracker, and/or an aromatic product stream from a steam cracker, wherein said aromatic product stream from a catalytic reformer, said aromatic product stream from a catalytic cracker, or said aromatic product stream from a steam cracker comprises at least 1 wppm to about 15 wt % non-aromatic hydrocarbons;
(f) contacting said toluene feedstock with a catalyst under toluene disproportionation conditions to product a toluene disproportionation product having light gases, Bz, PX, MX, OX, $C_9+$ and unreacted toluene, wherein said toluene disproportionating step has a toluene conversion ranging from about 15 to 35 wt % based on the toluene in said toluene feedstock, and wherein said toluene disproportionation product has a PX concentration of at least 70 wt % based on total xylenes in said toluene disproportionation product;
(g) separating at least a portion of said light gases, at least a portion of said Bz, and at least a portion of said unreacted toluene from said toluene disproportionation product to produce a $C_8+$ feedstock; and
(h) providing said $C_8+$ feedstock to a crystallization unit under crystallization conditions to produce a PX enriched stream having a PX concentration of at least 99.7 wt % based on the weight of said PX enriched stream, wherein said $C_8+$ feedstock has a PX concentration of at least 70 wt % based on total weight of xylenes in said $C_8+$ feedstock, which said $C_8+$ feedstock having a $C_9+$ hydrocarbons concentration in a range from 5000 wppm to 10 wt % based on the total weight of said $C_8+$ feedstock.

Paragraph 4. The process of paragraph 2 or 3, wherein step (b) comprises a hydrogen feed, wherein said toluene disproportionation conditions are toluene disproportion conditions, said toluene disproportion conditions comprise a temperature in a range from 100 to 700° C., a pressure in a range from 100 kPa-a to 10000 kPa-a; a WHSV in a range from 0.001 to 1000 $hr^{-1}$ based on the weight of said toluene in said toluene feedstock; a molar ratio of hydrogen over toluene in a range from 0.1 to 20.

Paragraph 5. The process of any one of paragraphs 2-4, wherein said $C_8+$ feedstock is supplied to a crystallization unit without separating $C_9+$ hydrocarbons from said $C_8+$ feedstock.

Paragraph 6. The process of any preceding paragraph, wherein said PX concentration of at least 85 wt % based on total weight of xylenes in said $C_8+$ feedstock.

Paragraph 7. The process of any preceding paragraph, wherein said PX concentration said PX enriched stream is at least 99.7 wt % based on the weight of said PX enriched stream.

Paragraph 8. The process of any preceding paragraph, wherein said $C_9+$ hydrocarbons concentration is in a range from 5000 wppm to 2 wt % based on the total weight of said $C_8+$ feedstock.

Paragraph 9. The process of any preceding paragraph, wherein said $C_8+$ feedstock further comprises naphthalene and said $C_8+$ feedstock has a naphthalene molar concentration of less than 10 mol % based on the total mole of the $C_8+$ hydrocarbons without PX.

Paragraph 10. The process of any preceding paragraph, wherein said crystallization unit is operated at a temperature of at least −30° C.

Paragraph 11. The process of any preceding paragraph, wherein said crystallization unit has a PX recovery of at least 85%.

Paragraph 12. The process of producing PX comprising providing a $C_8+$ feedstock, said $C_8+$ feedstock has $C_8$ hydrocarbons and $C_9+$ hydrocarbons, to a crystallization unit under crystallization conditions to produce a PX enriched stream having a PX concentration of at least 99.5 wt % based on the weight of said PX enriched stream, wherein said $C_8+$ feedstock is made by a STDP process consisting essentially of:
(i) a toluene purifying step to produce a toluene feedstock comprising at least 90 wt. % toluene and non-aromatic hydrocarbons ranging from 1 to 10 wt % based on the weight of said toluene feedstock; wherein said toluene purifying step has feed(s) comprises an aromatic product stream from a catalytic reformer, an aromatic product stream from a catalytic cracker, and/or an aromatic product stream from a steam cracker, wherein said aromatic product stream from a catalytic reformer, said aromatic product stream from a catalytic cracker, or said aromatic product stream from a steam cracker comprises at least 1 wppm to about 15 wt % non-aromatic hydrocarbons;
(j) contacting said toluene feedstock with a catalyst under toluene disproportionation conditions to product a toluene disproportionation product having light gases, Bz, PX, MX, OX, $C_9+$ and unreacted toluene, wherein said toluene disproportionating step has a toluene conversion ranging from about 15 to 35 wt % based on the toluene in said toluene feedstock, and wherein said toluene disproportionation product has a PX concentration of at least 70 wt % based on total xylenes in said toluene disproportionation product; and (k) separating at least a portion of said light gases, at least a portion of said Bz, and at least a portion of said unreacted toluene from said toluene disproportionation product to produce said $C_8+$ feedstock of any preceding paragraph.

Paragraph 13. An apparatus for producing a PX rich stream, which comprises:

(l) a reactor having an inlet and an outlet;

(m) a separation unit having an inlet and a first outlet and a second outlet, the inlet of the separation unit being fluidicly connected to the outlet of the reactor; and (n) a crystallization unit having an inlet, a first outlet, and a second outlet, the inlet of the crystallization unit being fluidicly connected to the second outlet of the separation unit.

Paragraph 14. The apparatus of paragraph 13, wherein said reactor is adapted for toluene disproportionation reaction, said inlet of the reactor is adapted to supplying a toluene feedstock comprising toluene to said reactor to form an effluent having $C_7-$ hydrocarbons, $C_8$ hydrocarbons, and $C_9+$ hydrocarbons; said outlet of the reactor is adapted to withdraw said effluent; wherein said separation unit is adapted to separate at least a portion of $C_7-$ hydrocarbons from said effluent to from a $C_8+$ feedstock, said $C_8+$ feedstock has a $C_9+$ hydrocarbons concentration from 1 wppm to 2 wt % based on the total weight of the $C_8+$ feedstock, said second outlet of said separation unit is adapted to withdraw said $C_8+$ feedstock; and wherein said crystallization unit is adapted to produce a PX enriched stream having a PX concentration of at least 99.5 wt % based on the weight of said PX enriched stream.

We claim:

1. In a process for producing para-xylene comprising selective toluene disproportionation to produce a stream comprising C7− hydrocarbons, xylenes, and C9+ hydrocarbons, and then recovery of para-xylene by crystallization, including a step of removal of said C7− hydrocarbons from said stream prior to said crystallization, the improvement comprising the absence a step of removal of C9+ hydrocarbons between said selective toluene disproporationation and said crystallization.

2. A process of producing para-xylene comprising:

(a) providing a toluene feedstock having toluene to a reaction zone;

(b) contacting said toluene with a catalyst under toluene disproportionation conditions to form an effluent having $C_7-$ hydrocarbons, $C_8$ hydrocarbons and $C_9+$ hydrocarbons, wherein said $C_8$ hydrocarbons comprise para-xylene, meta-xylene, and ortho-xylene, wherein said effluent has a para-xylene concentration of at least 70 wt % based on total weight of xylenes in said effluent;

(c) separating at least a portion of $C_7-$ hydrocarbons from said effluent to form a $C_8+$ feedstock, wherein said $C_8+$ feedstock has a $C_9+$ hydrocarbons concentration from 1 wppm to 10 wt % based on the total weight of the $C_8+$ feedstock; and (d) supply at least a portion of said $C_8+$ feedstock to a crystallization unit under crystallization conditions to produce a para-xylene enriched stream having a para-xylene concentration of at least 99.5 wt % based on the weight of said para-xylene enriched stream.

3. The process of claim 2, wherein step (b) comprises a hydrogen feed, wherein said toluene disproportionation conditions are toluene disproportionation conditions, said toluene disproportion conditions comprise a temperature in a range from 100 to 700° C., a pressure in a range from 100 kPa-a to 10000 kPa-a; a WHSV in a range from 0.001 to 1000 hr$^{-1}$ based on the weight of said toluene in said toluene feedstock; a molar ratio of hydrogen over toluene in a range from 0.1 to 20.

4. The process of claim 2, wherein said toluene disproportionation conditions comprise a temperature in a range from 400 to 550° C., a pressure in a range from 200 kPa-a to 5000 kPa-a; a WHSV in a range from 0.01 to 100 hr$^{-1}$ based on the weight of said toluene in said toluene feedstock; a molar ratio of hydrogen over toluene in a range from 0.5 to 10.

5. The process of claim 2, wherein said toluene disproportionation conditions comprise a temperature in a range from 400 to 500° C., a pressure in a range from 200 kPa-a to 2800 kPa-a; a WHSV in a range from 2 to 10 hr$^{-1}$ based on the weight of said toluene in said toluene feedstock; a molar ratio of hydrogen over toluene in a range from 0.8 to 5.

6. The process of claim 2, wherein said para-xylene concentration of at least 75 wt % based on total weight of xylenes in said $C_8+$ feedstock.

7. The process of claim 2, wherein said para-xylene concentration of at least 80 wt % based on total weight of xylenes in said $C_8+$ feedstock.

8. The process of claim 2, wherein said $C_9+$ hydrocarbons concentration is in a range from 1000 wppm to 2 wt % based on the total weight of said $C_8+$ feedstock.

9. The process of claim 2, wherein said $C_9+$ hydrocarbons concentration is in a range from 5000 wppm to 1 wt % based on the total weight of said $C_8+$ feedstock.

10. The process of claim 2, wherein said crystallization unit is operated at a temperature of at least −25° C.

11. The process of claim 9, wherein said crystallization unit has a para-xylene recovery of at least 85%.

12. The process of claim 2, wherein said $C_8+$ feedstock is supplied to a crystallization unit without separating $C_9+$ hydrocarbons from said $C_8+$ feedstock.

13. A process of producing para-xylene consisting essentially of:

(a) a toluene purifying step to produce a toluene feedstock comprising at least 90 wt % toluene and non-aromatic hydrocarbons ranging from 1 to 10 wt % based on the weight of said toluene feedstock; wherein said toluene purifying step has feed(s) comprising an aromatic product stream from a catalytic reformer, an aromatic product stream from a catalytic cracker, and/or an aromatic product stream from a steam cracker, wherein said aromatic product stream from a catalytic reformer, said aromatic product stream from a catalytic cracker, or said aromatic product stream from a steam cracker comprising at least 1 wppm to about 15 wt % non-aromatic hydrocarbons;

(b) contacting said toluene feedstock with a catalyst under toluene disproportionation conditions to produce a toluene disproportionation product having light gases, benzene, para-xylene, meta-xylene, ortho-xylene, C9+ and unreacted toluene, wherein said toluene disproportionating step has a toluene conversion ranging from about 15 to 35 wt % based on the toluene in said toluene feedstock, and wherein said toluene disproportionation product has a para-xylene concentration of at least 70 wt % based on total xylenes in said toluene disproportionation product;

(c) separating at least a portion of said light gases, at least a portion of said benzene, and at least a portion of said unreacted toluene from said toluene disproportionation product to produce a $C_8+$ feedstock; and (d) providing said $C_8+$ feedstock to a crystallization unit under crystallization conditions to produce a para-xylene enriched stream having a para-xylene concentration of at least 99.7 wt % based on the weight of said para-xylene enriched stream, wherein said $C_8+$ feedstock has a para-xylene concentration of at least 70 wt % based on total weight of xylenes in said $C_8+$ feedstock, which said $C_8+$ feedstock having a $C_9+$ hydrocarbons concentration in a range from 5000 wppm to 10 wt % based on the total weight of said $C_8+$ feedstock.

* * * * *